United States Patent [19]
Froshauer et al.

[11] Patent Number: 5,981,762
[45] Date of Patent: Nov. 9, 1999

[54] SUBSTITUTED INDOLE-2-CARBOXYLIC ACIDS AS GLUCOSYL TRANSFERASE INHIBITORS

[75] Inventors: Susan A. Froshauer, Guilford; Steven W. Goldstein, Noank; William G. Stirtan, East Lyme, all of Conn.

[73] Assignee: Pfizer Inc., New York, N.Y.

[21] Appl. No.: 09/122,855

[22] Filed: Jul. 28, 1998

Related U.S. Application Data

[60] Provisional application No. 60/054,140, Jul. 29, 1997.

[51] Int. Cl.$^6$ .................................................. C07D 209/12
[52] U.S. Cl. ............................................................. 548/493
[58] Field of Search ...................................... 548/492, 493

[56] References Cited

PUBLICATIONS

Avromenko et al., "Indole Derivatives. LIV. Synthesis of 3,5–Diacetylindole." Chem. Heterocycl. Compd., vol. 6 (1970), p. 1131.

Ruhemann, S; Blackman, F., "LX. Benzophenylhydrazine." J. Chem. Soc., vol. 55 (1889), p. 617.

Chem. Pharm. Bull. 38(12) 3261–3267 (1990), Masanobu Tani etal.: "Synthetic Studies on Indoles and Related Compounds. XXV. The Friedel–Crafts Acylation of Ethyl 1H–Indole–2–carboxylate."

Database Xfire Beilstein Reg. No. 384515 XP002079476.

Warner–Lambert Research Institute, Morris Plains, New Jersey, Maximillan Von Strandtmann, et al.: "Acltryptamines III. 5–Acetyltryptophan and Related Compounds."

*Biochemistry*, 1989, 28, 8108–8116, "Glucosylation of Glycoproteins by Mammalian, Plant, Fungal, and Trypanosomatid Protozoa Microsomal Membranes".

*Primary Examiner*—John M. Ford
*Attorney, Agent, or Firm*—Peter C. Richardson; Gregg C. Benson; Mervin E. Brokke

[57] ABSTRACT

Indole carboxylic acids are useful as UGGTASE inhibitors.

2 Claims, No Drawings

SUBSTITUTED INDOLE-2-CARBOXYLIC ACIDS AS GLUCOSYL TRANSFERASE INHIBITORS

This application is a continuation of Provisional Application 60/054,140, filed Jul. 29, 1997.

This invention relates to substituted indole-2-carboxylic acids and their use as inhibitors of uridine diphosphate glucose glucosyltransferase in mammals.

BACKGROUND OF THE INVENTION

Uridine diphosphate glucose: glycoprotein glucosyltransferase (UGGTase) is an enzyme found in the endoplasmic reticulum which catalyzes the glucosylation of glycoproteins containing glucose free high mannose oligosaccharides. UGGTase is a key enzyme in the calnexin/calreticulin cycle acting as a protein folding sensor. Those glycoproteins which are misfolded or incompletely folded are selectively glucosylated by UGGTase such that they remain ligands for calnexin/calreticulin and remain in the endoplasmic reticulum until properly folded. Inhibitors of UGGTase may be used to treat several pathological conditions including viral infection, cystic fibrosis, emphysema, scurvy, hereditary hyperlipemia, Glanzman's thromobostenia, congenital sucrose-isomaltese deficiency, hexosaminidase A deficiency, Marfan's syndrome, fibrinogen storage disease, nanomelia (in chicken), α-antichymotrypsin deficiency, von Willebrand's disease, retinitis pigmentosa, and glioblastoma.

SUMMARY OF THE INVENTION

This invention provides a compound of formula I

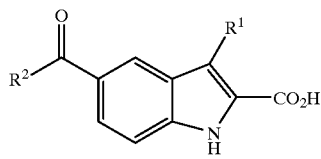

wherein:
$R^1$ is hydrogen or ($C_1$–$C_6$) alkyl; and
$R^2$ is ($C_1$–$C_6$) alkyl, ($C_3$–$C_7$) cycloalkyl, phenyl or phenyl substituted with one to three groups independently selected from ($C_1$–$C_3$) alkyl, ($C_1$–$C_3$) alkoxy, halogen, cyano or nitro; or a pharmaceutical acceptable salt thereof.

In another aspect this invention provides a method for treating a disease or condition in a mammal which is caused by UGGTase which comprises treating a mammal in need of such treatment with an effective amount of a compound of formula I or a pharmaceutically acceptable salt or prodrugs thereof.

In a further aspect, this invention provides a method of treating a pathological condition selected from the group consisting of viral infection, cystic fibrosis, emphysema, scurvy, hereditary hyperlipemia, Glanzman's thromobostenia, congenital sucrose-isomaltese deficiency, hexosaminidase A deficiency, Marfan's syndrome, fibrinogen storage disease, nanomelia (in chicken), α-antichymotrypsin deficiency, von Willebrand's disease, retinitis pigmentosa, and glioblastoma; which comprises administering to a mammal in need of such treatment a compound of Formula I.

Indole 2-carboxylate esters optionally substituted with lower alkyl groups in the 3-position are available from commercial sources or are prepared by known methods from readily available starting materials.

Compounds of formula I are prepared by reacting the appropriate indole 2-carboxylate ester with acylhalides in a reaction inert solvent in the presence of aluminum chloride. The product is isolated by conventional means. The desired 5-carbonylaryl or alkyl-indole-2-carboxylic acid is obtained by hydrolysis of the ester preferably by a base such as LiOH in a suitable solvent such as THF. After acidification, the product is isolated by conventional means.

Representative compounds used in the present method, which are encompassed by Formula I include their pharmaceutically acceptable salts. Non-toxic pharmaceutically acceptable salts include salts of bases such as lithium hydroxide, sodium hydroxide, calcium hydroxide or substituted amine compounds and the like. Those skilled in the art will recognize a wide variety of non-toxic pharmaceutically acceptable addition salts.

The compounds of general formula I may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition, there is provided a pharmaceutical formulation comprising a compound of general formula I and a pharmaceutically acceptable carrier. One or more compounds of general formula I may be present in association with one or more non-toxic pharmaceutically acceptable carriers and/or diluents and/or adjuvants and if desired other active ingredients. The pharmaceutical compositions containing compounds of general formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium go carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of general formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compounds of general formula I may be administered parenterally in a sterile medium, The drug, depending on the vehicle and concentration used can either be suspended or dissolved in the vehicle. Advantageously, adjuvants such as local anesthetics, preservatives and buffering agents can be dissolved in the vehicle.

Dosage levels of the order of from about 0.1 mg to about 50 mg per kilogram of body weight per day in a single or dovided doses are useful in the treatment of the above-indicated conditions (about 1 mg to about 500 g per patient per day). The amount of active ingredient that may be combined with the carrier materials to produce a single dosage form will vary depending upon the host treated and the particular mode of administration. Dosage unit forms will generally contain between from about 1 mg to about 250 mg of an active ingredient It will be understood, however, that the specific dose level for any particular patient will depend upon a variety of factors including the activity of the specific compound employed, the age, body weight, general health, sex, diet, time of administration, route of administration and rate of excretion, drug combination and the severity of the particular disease undergoing therapy.

As a consequence of their action in treating pathological conditions the compounds of the present invention possess utility for treatment of ungulate animals such as swine, cattle, sheep, and goats, and poultry. Compounds of formula I can additionally be used for the treatment of household pets, for example companion animals such as dogs and cats. The administration of a compound of formula I can be effected orally or parenterally. An amount of a compound of formula I is administered such that an effective dose is received, generally a daily dose which, when administered orally to an animal is usually between 0.01 and 20 mg/kg of body weight, preferably between 0.05 and 10 mg/kg of body weight. Conveniently, the medication can be carried in drinking water so that a therapeutic dosage of the agent is ingested with the daily water supply. The agent can be directly metered into drinking water, preferably in the form of a liquid, water-soluble concentrate (such as an aqueous solution of a water soluble salt).

Conveniently, the active ingredient can also be added directly to the feed, as such, or in the form of an animal feed supplement, also referred to as a premix or concentrate. A premix or concentrate of therapeutic agent in a carrier is more commonly employed for the inclusion of the agent in the feed. Suitable carriers are liquid or solid, as desired, such as water, various meals such as alfalfa meal, soybean meal, cottonseed oil meal, linseed oil meal, corncob meal and corn meal, molasses, urea, bone meal, and mineral mixes such as are commonly employed in poultry feeds. A particularly effective carrier is the respective animal feed itself; that is, a small portion of such feed. The carrier facilitates uniform distribution of the active materials in the finished feed with which the premix is blended. It is important that the compound be thoroughly blended into the premix and, subsequently, the feed. In this respect, the agent may be dispersed or dissolved in a suitable oily vehicle such as soybean oil, corn oil, cottonseed oil, and the like, or in a volatile organic solvent and then blended with the carrier. It will be appreciated that the proportions of active material in the concentrate are capable of wide variation since the amount of agent in the finished feed may be adjusted by blending the appropriate proportion of premix with the feed to obtain a desired level of therapeutic agent.

High potency concentrates may be blended by the feed manufacturer with proteinaceous carrier such as soybean oil meal and other meals, as described above, to produce concentrated supplements which are suitable for direct feeding to animals. In such instances, the animals are permitted to consume the usual diet.

Alternatively, such concentrated supplements may be added directly to the feed to produce a nutritionally balanced, finished feed containing a therapeutically effective level of a compound according to the invention. The mixtures are thoroughly blended by standard procedures, such as in a twin shell blender, to ensure homogeneity.

If the supplement is used as a top dressing for the feed, it likewise helps to ensure uniformity of distribution of the active material across the top of the dressed feed.

Drinking water and feed effective for treating domestic animals are generally prepared by mixing a compound of the invention with a sufficient amount of animal feed to provide from about $10^{-3}$ to 500 ppm of the compound in the feed or water.

The preferred medicated swine, cattle, sheep and goat feeds generally contain from 1 to 400 grams of active ingredient per ton of feed, the optimum amount for these animals usually being about 50 to 300 grams per ton of feed.

The preferred poultry and domestic pet feeds usually contain about 1 to 400 grams and preferably 10 to 400 grams of active ingredient per ton of feed.

For parenteral administration in animals, the compounds of the present invention may be prepared in the form of a paste or a pellet and administered as an implant, usually under the skin of the head or ear of the animal in which increase in lean meat deposition and improvement in lean mean to fat ratio is sought.

In general, parenteral administration involves injection of a sufficient amount of the compounds of the present invention to provide the animal with 0.01 to 20 mg/kg/day of body weight of the active ingredient. The preferred dosage for poultry, swine, cattle, sheep, goats and domestic pets is in the range of from 0.05 to 10 mg/kg/day of body weight of active ingredient.

EXAMPLES

Example 1

Ethyl 5-carbonylphenyl-3-methyl-indole-2-caboxylate

To a solution of ethyl 3-methyl-indole-2-carboxylate (1.5 g, 7.9 mmol) and dichloroethane (20 mL) was added a solution of benzoyl chloride (2.23 g, 15.9 mmol) and dichloroethane (10 mL). Anhydrous aluminum trichloride (2.1 g, 15.8 mmol) was added in one portion and the reaction mixture was heated to reflux for 4 hours. The mixture was then poured over ice and neutralized with potassium acetate. The organic layer was separated, washed with a 5% solution of NaHCO$_3$ and dried over MgSO$_4$. The organic solution was then filtered, concentrated and subjected to silica gel chromatography with ethyl acetate—hexanes mixtures as eluent to provide the title compound (0.94 g). Recrystallization from benzene gave a yellow solid (mp 180–181° C.).

Example 2

5-Carbonylphenyl-3-methyl-indole-2-carboxylic acid

To a solution of ethyl 5-carbonylphenyl-3-methyl-indole-2-carboxylate (10 mg, 0.034 mmol) and THF (0.5 mL) was added a solution of LiOH (3.6 mg, 0.15 mmol) and water (0.2 mL). The solution was stirred for 6 h, poured into a mixture of 1 N HCl (1 mL) and ethyl acetate (2 mL). The organic layer was separated, the aqueous layer extracted with ethyl acetate and the combined organic layers was washed with water (1 mL). The solution was dried (MgSO$_4$), filtered and concentrated to give the title compound as a white solid.

$^1$H NMR (400 Mhz, CDCl$_3$/MeOH d$_4$) 8.08 (d, J=1 Hz, 0.7H), 7.75 (m, 3H), 7.60 (t, J=7.2 Hz, 1H), 7.5 (m, 3H), 2.56 (s, 3H).

MS (APCI, positive mode) 280 (100, M+)

Example 3

UGGTase Assay

Materials:

Uridine diphospho-D-[1-$^3$H]glucose was obtained from Amersham Life Science, Inc. Bovine thyroglobulin and buffer chemicals were obtained from Sigma.

Methods:

Denatured bovine thyroglobulin was prepared as described previously (Trombetta et al., 1989). UGGTase assays (100 µL) were carried out at room temperature for 60 minutes in assay buffer (10 mM HEPES, pH 7.5, 10 mM CaCl$_2$) containing uridine diphospho-D-[1-$^3$H]glucose (5.3 mCi/µmol; ~5×10$^5$ cpm/assay), denatured bovine thyroglobulin (0.75 mg/mL), and compound (4.5 µM). Reactions were initiated with UGGTase (2 nM), and terminated with TCA (10%). The product of the enzyme catalyzed reaction, radiolabeled thryoglobulin, was captured on a glass fiber filtermat and analyzed in a scintillation counter.

Reference

1) Trombetta, S. E., Bosch, M., & Parodi, A. J. (1989) Biochemistry, 28, 8108–8116.

We claim:

1. A compound of the formula

wherein R$^1$ is (C$_1$–C$_3$) alkyl and R$^2$ is phenyl, or a pharmaceutically acceptable salt thereof.

2. The compound of claim 1 wherein R$^1$ is methyl.

* * * * *